(12) United States Patent
Romig et al.

(10) Patent No.: US 8,997,558 B2
(45) Date of Patent: Apr. 7, 2015

(54) COMBUSTOR PROBE FOR GAS TURBINE

(75) Inventors: Bryan Wesley Romig, Simpsonville, SC (US); Jonathan Hale Kegley, Greer, SC (US); Robert Wade Clifford, Duncan, SC (US); Derrick Walter Simons, Greer, SC (US)

(73) Assignee: General Electric Company, Schenectady, NY (US)

( * ) Notice: Subject to any disclaimer, the term of this patent is extended or adjusted under 35 U.S.C. 154(b) by 646 days.

(21) Appl. No.: 13/075,055

(22) Filed: Mar. 29, 2011

(65) Prior Publication Data

US 2012/0247108 A1 Oct. 4, 2012

(51) Int. Cl.
*G01M 15/05* (2006.01)
*G01N 1/22* (2006.01)
*F01D 21/00* (2006.01)

(52) U.S. Cl.
CPC ............ *G01N 1/2252* (2013.01); *F01D 21/003* (2013.01); *F05D 2270/80* (2013.01)

(58) Field of Classification Search
CPC ..................................................... G01L 23/24
USPC .................. 73/866.5, 112.01, 112, 5, 114.31
See application file for complete search history.

(56) References Cited

U.S. PATENT DOCUMENTS

| 4,101,404 | A | 7/1978 | Blumenthal et al. |
| 4,537,661 | A | 8/1985 | Lee et al. |
| 4,808,294 | A * | 2/1989 | Beuret et al. ................. 204/427 |
| 6,550,336 | B2 * | 4/2003 | Brehm et al. ................... 73/707 |
| 6,857,320 | B2 * | 2/2005 | Gleeson et al. ................. 73/756 |
| 6,978,680 | B2 | 12/2005 | Gleeson et al. |
| 2002/0053233 | A1 * | 5/2002 | Grieser et al. ............. 73/31.05 |
| 2002/0103547 | A1 | 8/2002 | Nomura et al. |

FOREIGN PATENT DOCUMENTS

| CN | 101568832 A | 10/2009 |
| CN | 101782234 A | 7/2010 |

OTHER PUBLICATIONS

Chinese Office Action issued Dec. 31, 2014 for Chinese Application No. 201210102483.7, 7 pages.

* cited by examiner

*Primary Examiner* — Paul West
(74) *Attorney, Agent, or Firm* — Fletcher Yoder, P.C.

(57) ABSTRACT

Embodiments of the present disclosure are directed towards a turbine combustor probe having a combustion dynamics monitoring probe configured to monitor combustion dynamics within a turbine combustor. The turbine combustor probe also has a gas sampling sleeve configured to collect a gas sample from an airflow path between a liner and a flow sleeve of the turbine combustor.

20 Claims, 4 Drawing Sheets

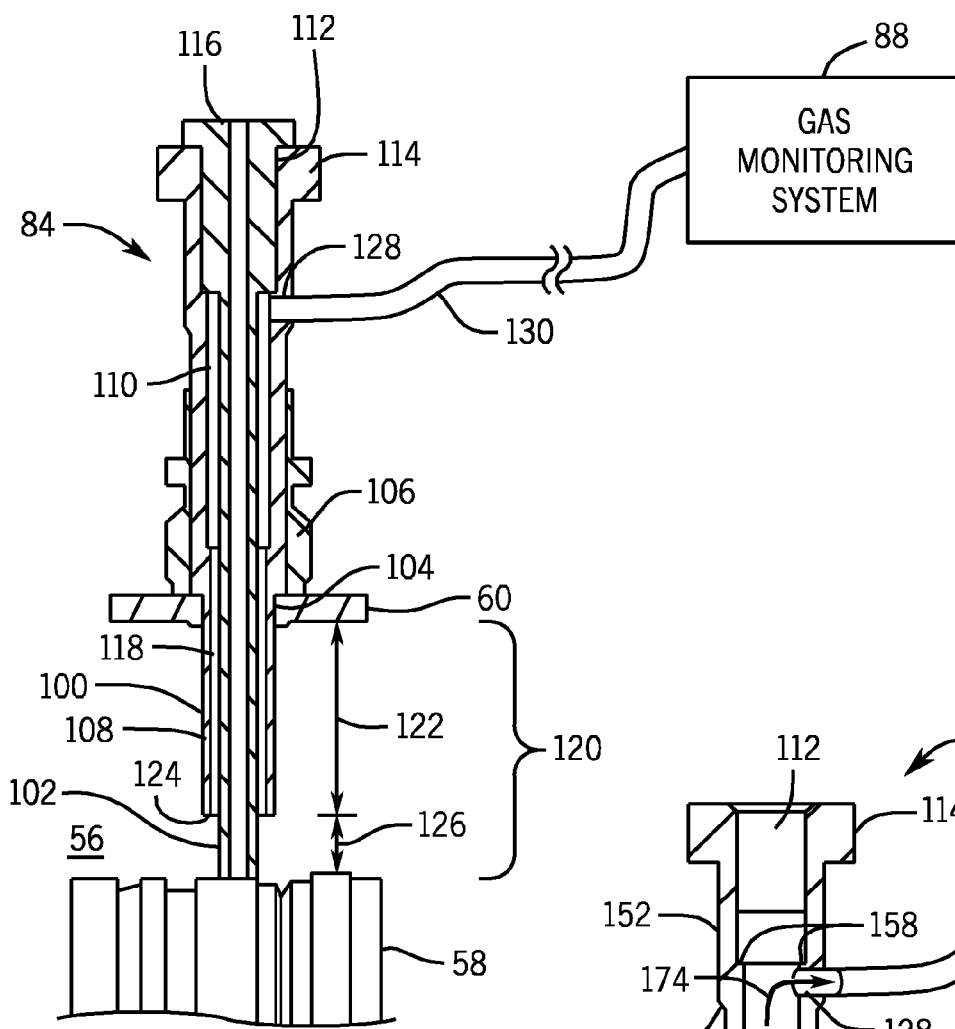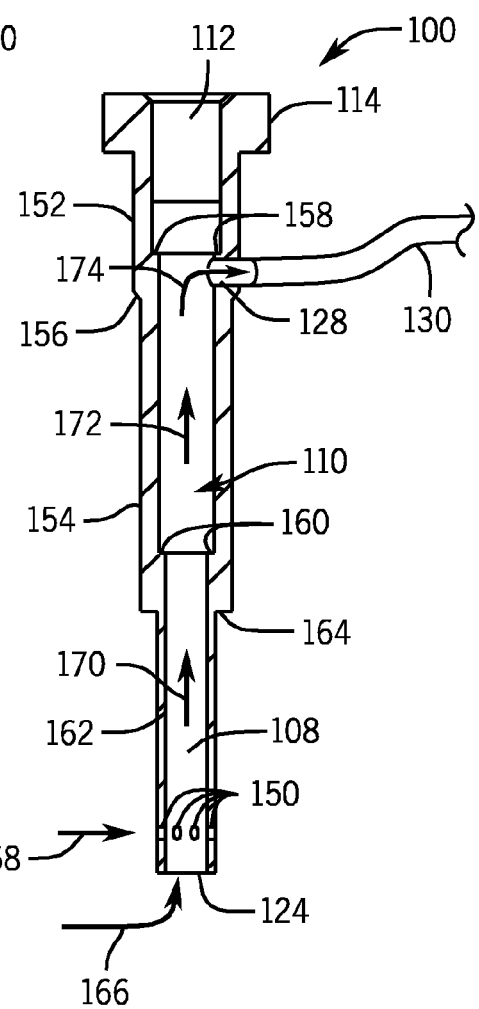
FIG. 3
FIG. 4

COMBUSTOR PROBE FOR GAS TURBINE

BACKGROUND OF THE INVENTION

The subject matter disclosed herein relates to combustors, and, more particularly, to a gas sampling sleeve for a combustor probe.

Gas turbine systems typically include at least one gas turbine engine having a compressor, a combustor, and a turbine. The combustor may have a primary combustion system and a secondary combustion system downstream from the primary combustion system, which may be referred to as a late lean injection (LLI) system. In combustors having a LLI system, fuel is routed into the secondary combustion system of the gas turbine system through the compressor discharge and into a transition piece. If the fuel routing system delivering fuel to the secondary combustion system were to leak, a fuel/air mixture could develop within the compressor discharge. A leak in the LLI fuel delivery and/or a fuel/air mixture within the compressor discharge may need to be detected quickly to allow repairs to be made to the LLI fuel delivery system.

BRIEF DESCRIPTION OF THE INVENTION

Certain embodiments commensurate in scope with the originally claimed invention are summarized below. These embodiments are not intended to limit the scope of the claimed invention, but rather these embodiments are intended only to provide a brief summary of possible forms of the invention. Indeed, the invention may encompass a variety of forms that may be similar to or different from the embodiments set forth below.

In a first embodiment, a system includes a turbine combustor and a combustor probe, where the combustor probe includes a combustion dynamics monitoring probe configured to monitor combustion dynamics within the turbine combustor and a gas sampling sleeve configured to collect a gas sample from an airflow path between a liner and a flow sleeve of the turbine combustor.

In a second embodiment, a turbine combustor probe includes a gas sampling sleeve configured to collect a gas sample from an air flow in a turbine combustor and a combustion dynamics probe configured to monitor combustion dynamics in the turbine combustor. The combustion dynamics probe is disposed within the gas sampling sleeve, and an annular passage is disposed between the combustion dynamics probe and the gas sampling device.

In a third embodiment, a turbine combustor probe sleeve includes a gas sampling tube operatively coupled to a gas sample cavity, where the gas sampling tube and the gas sample cavity are configured to receive a combustor probe and to collect a gas sample from an air flow in a turbine combustor.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIG. 3 is a cross-sectional side view of an embodiment of a combustor probe, taken along line 3-3 of FIG. 2, having a combustion dynamics monitoring probe and a gas sampling sleeve partially disposed between a liner and a flow sleeve of the combustor;

FIG. 4 is a cross-sectional side view of an embodiment of a combustor probe sleeve configured to receive a combustion dynamics monitoring probe and collect a gas sample from a combustor;

DETAILED DESCRIPTION OF THE INVENTION

Figure 1:
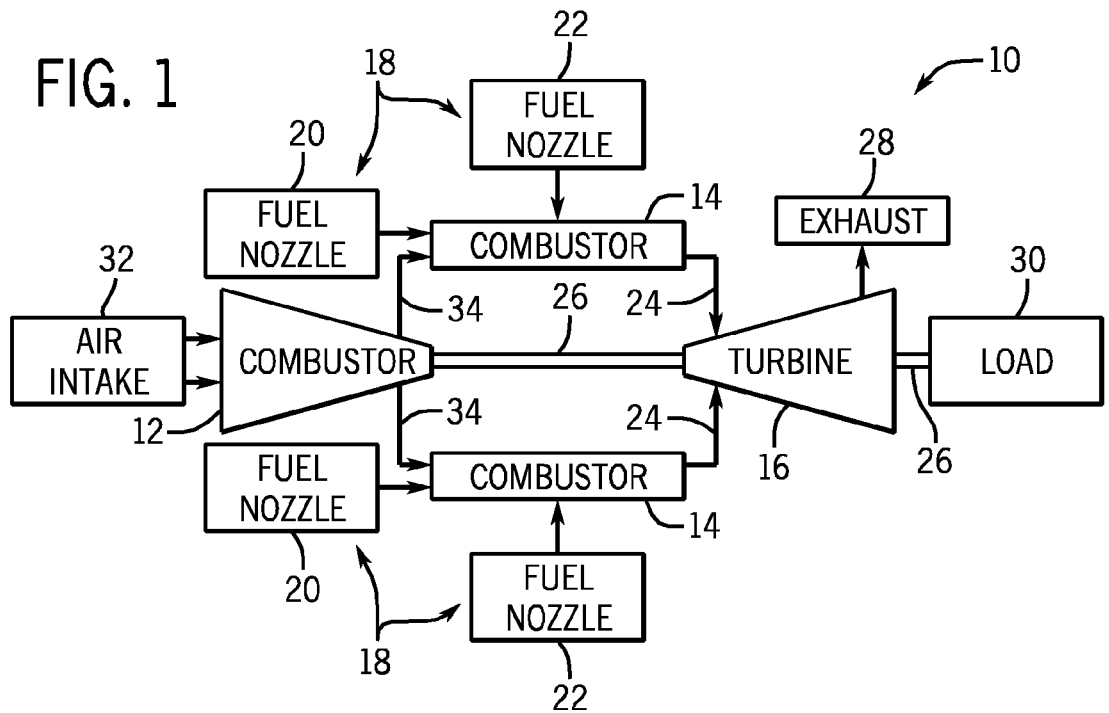
FIG. 1 is a schematic of an embodiment of a gas turbine system including two turbine combustors which each may include a combustor probe having a combustion dynamics monitoring probe and a gas sampling sleeve.

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

The present disclosure is directed towards a gas turbine combustor probe having a combustion dynamics monitoring probe and a gas sampling sleeve disposed around the combustion dynamics monitoring probe. As mentioned above, gas turbine systems include turbine combustors which may include a LLI system for secondary combustion. A fuel supply system may route fuel to the LLI system through a compressor discharge. A leak in the fuel supply system could cause an air/fuel mixture to form in the compressor discharge, which may require maintenance or service to be performed on the gas turbine system. Due to the nature of the flow in and around the compressor discharge, any fuel leaked from the LLI fuel supply system in the compressor discharge should be quickly swept towards the head end of the turbine combustor.

In particular, the fuel travels toward the head end of the turbine combustor through the annulus between the flow sleeve and the liner of the turbine combustor.

Certain embodiments of the present disclosure include a dual purpose combustor probe configured to detect the presence of fuel in the combustor air flow, providing for rapid leak detection in the LLI fuel supply system. For example, the combustor probe may be located near the head end of the turbine combustor. In one embodiment, the combustor probe is a dual purpose combustor probe that includes a gas sampling sleeve which may be configured to support a combustion dynamics monitoring probe. For example, the combustion dynamics monitoring probe may be configured to monitor pressure variations and/or flow rates within the turbine combustor. Additionally, the gas sampling sleeve may be disposed around the combustion dynamics monitoring probe. In certain embodiments, combustors already having a combustion dynamics monitoring probe may be retrofitted to include the gas sampling sleeve for detecting a leak in the fuel supply system of the LLI system. More specifically, the gas sampling sleeve may be sized such that it fits within a preexisting probe port, through which a probe holder holding the combustion dynamics monitoring probe previously fit. By retrofitting an existing combustion dynamics monitoring probe (and associated probe holder) and using an existing probe port in the turbine combustor, the need for a substantial or significant redesign of existing combustion casings (e.g., adding a new probe port) may be reduced or eliminated.

Turning now to the drawings, FIG. 1 illustrates a block diagram of an embodiment of a gas turbine system 10. The diagram includes a compressor 12, turbine combustors 14, and a turbine 16. The turbine combustors 14 include fuel nozzles 18 which route a liquid fuel and/or gas fuel, such as natural gas or syngas, into the turbine combustors 14. As shown, each turbine combustor 14 may have multiple fuel nozzles 18. More specifically, the turbine combustors 14 may each include a primary fuel injection system having primary fuel nozzles 20 and a secondary fuel injection system having secondary fuel nozzles 22. As described in detail below, each turbine combustor 14 may also include a combustor probe having a combustion dynamics monitoring probe and a gas sampling sleeve.

The turbine combustors 14 ignite and combust an air-fuel mixture, and then pass hot pressurized combustion gasses 24 (e.g., exhaust) into the turbine 16. Turbine blades are coupled to a shaft 26, which is also coupled to several other components throughout the turbine system 10. As the combustion gases 24 pass through the turbine blades in the turbine 16, the turbine 16 is driven into rotation, which causes the shaft 26 to rotate. Eventually, the combustion gases 24 exit the turbine system 10 via an exhaust outlet 28. Further, the shaft 26 may be coupled to a load 30, which is powered via rotation of the shaft 26. For example, the load 30 may be any suitable device that may generate power via the rotational output of the turbine system 10, such as a power generation plant or an external mechanical load. For instance, the load 30 may include an electrical generator, a propeller of an airplane, and so forth.

In an embodiment of the turbine system 10, compressor blades are included as components of the compressor 12. The blades within the compressor 12 are coupled to the shaft 26, and will rotate as the shaft 26 is driven to rotate by the turbine 16, as described above. The rotation of the blades within the compressor 12 compress air from an air intake 32 into pressurized air 34. The pressurized air 34 is then fed into the fuel nozzles 18 of the combustors 14. The fuel nozzles 18 mix the pressurized air 34 and fuel to produce a suitable mixture ratio for combustion (e.g., a combustion that causes the fuel to more completely burn) so as not to waste fuel or cause excess emissions.

Figure 2:
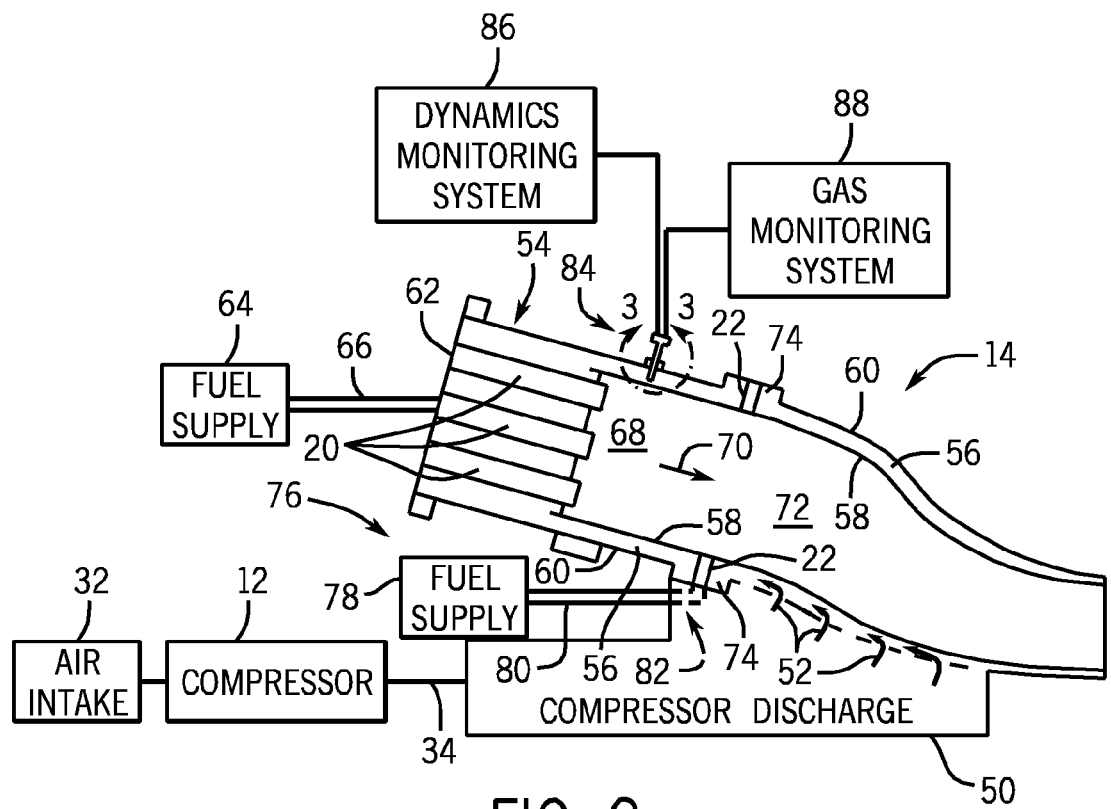
FIG. 2 is a cross-sectional side view of an embodiment of one of the turbine combustors of FIG. 1 including a combustor probe having a combustion dynamics monitoring probe and a gas sampling sleeve.

FIG. 2 is a schematic of an embodiment of one of the combustors 14 of FIG. 1, including a combustor probe having a gas sampling sleeve and a combustion dynamics monitoring probe. As described above, the compressor 12 receives air from an air intake 32, compresses the air, and produces a flow of pressurized air 34 for use in the combustion process within the combustor 14. As shown in the illustrated embodiment, the pressurized air 34 is received by a compressor discharge 50 that is operatively coupled to the turbine combustor 14. As shown by arrows 52, the pressurized air 34 flows from the compressor discharge 50 towards a head end 54 of the combustor 14. More specifically, the pressurized air flows through an annulus 56 between a liner 58 and a flow sleeve 60 of the turbine combustor 14 to reach the head end 54.

In certain embodiments, the head end 54 includes a cover plate 62 that may support the primary fuel nozzles 20 depicted in FIG. 1. In the illustrated embodiment, a primary fuel supply 64 provides fuel 66 to the primary fuel nozzles 20. Additionally, the primary fuel nozzles 20 receive the pressurized air 34 from the annulus 56 of the turbine combustor 14. The primary fuel nozzles 20 combine the pressurized air 34 with the fuel 66 provided by the primary fuel supply 64 to form an air/fuel mixture that is ignited and combusted in a primary combustion zone 68 of the turbine combustor 14 to form combustion gases (e.g., exhaust). The combustion gases flow in a direction 70 to a secondary combustion zone 72. At the secondary combustion zone 72, a LLI system 74 provides secondary fuel to the stream of combustion gases. In the illustrated embodiment, a secondary fuel system 76 includes a secondary fuel supply 78, which provides secondary fuel 80 to the LLI system 74 (e.g., through the secondary fuel nozzles 22 depicted in FIG. 1). As indicated by reference numeral 82, in certain embodiments, the secondary fuel 80 is routed through the compressor discharge 50. As described above, a leak in the secondary fuel system 76 may cause an air/fuel mixture to develop within the compressor discharge 50. In the event of a leak, the combustor 14 and the gas turbine system 10 may need to be shut down for maintenance and repair. As a result, it may be beneficial to have a system for rapid detection of a leak in the secondary fuel system 76.

To detect a leak in the secondary fuel system 76, in certain embodiments, the combustor 14 includes a combustor probe 84. The combustor probe 84 may be referred to as a dual purpose combustor probe. For example, the combustor probe 84 may include a gas sampling sleeve and a combustion dynamics monitoring probe. As such, the dual purpose combustor probe 84 may be capable of monitoring combustion dynamics within the turbine combustor 14 (e.g., inside the combustion zone 68), as well as receiving gas samples along the air flow path, which may be used to determine if fuel is leaking through the annulus 56 between the flow sleeve 60 and the liner 58 of the turbine combustor 14. As shown, the combustor probe 84 penetrates the flow sleeve 60 near the head end 54 of the turbine combustor 14 and is at least partially disposed in the annulus 56 between the flow sleeve 60 and the liner 58. As described above, the nature of the flow from the compressor discharge 50 directs the pressurized air 34 from the compressor discharge 50 through the annulus 56 and towards the head end 54. Consequently, any fuel leaking into the compressor discharge 50 from the secondary fuel supply 76 may be detected in the annulus 56 near the head end 54 of the turbine combustor 14.

More specifically, as described in greater detail below, the combustor probe 84 may include a gas sampling sleeve configured to collect a gas sample from the annulus 56. The gas sampling sleeve may also be configured to receive and support a combustion dynamics monitoring probe for measuring and acquiring data such as dynamic pressure within the turbine combustor 14. For example, the combustion dynamics monitoring probe may be a wave guide configured to transmit a pressure signal from the turbine combustor 14 to a dynamics monitoring system 86 coupled to the combustor probe 84. For example, the dynamics monitoring system 86 may include one or more inputs configured to receive a lead from the combustor probe 84. The dynamics monitoring system 86 may further include a processor and memory circuitry having computer instructions encoded thereon, which are configured to analyze various combustion dynamics parameters. Additionally, in certain embodiments, the dynamics monitoring system 86 may include a user interface with a display for communicating system information and analysis results to a user or operator.

In the illustrated embodiment, the combustor probe 84 is also coupled to a gas monitoring system 88. The gas monitoring system 88 may receive a gas sample collected by the gas sampling sleeve of the combustor probe 84 from the annulus 56 of the turbine combustor 14. More specifically, the gas monitoring system 88 may include one or more inputs configured to receive a lead from the combustor probe 84. The gas monitoring system 88 may also include a processor and memory circuitry having computer instructions encoded thereon, which are configured to analyze various characteristics of the gas sample received from the combustor probe 84. For example, encoded computer instructions of the gas monitoring system 88 may be configured to detect the presence of fuel in the gas sample. The encoded computer instructions of the gas monitoring system 88 may also be configured to monitor other properties of the gas sample, such as gas composition, gas temperature, and so forth.

FIG. 3 is a cross-sectional side view of an embodiment of the combustor probe 84 of FIG. 2, taken along line 3-3 of FIG. 2, illustrating a gas sampling sleeve 100 and a combustion dynamics monitoring probe 102. In the illustrated embodiment, the combustor probe 84 is at least partially disposed within the annulus 56 between the flow sleeve 60 and the liner 58 through an aperture 104 in the flow sleeve 60 of the turbine combustor 14. As shown, the combustor probe 84 is secured to the flow sleeve 60 and held in place by a probe holder 106.

In the illustrated embodiment, the combustion dynamics monitoring probe 102 is disposed within the gas sampling sleeve 100. Specifically, the gas sampling sleeve 100 includes a gas sampling tube 108 and a gas cavity 110, which receive the combustion dynamics monitoring probe 102 through an opening 112 at a top portion 114 of the gas sampling sleeve 100. In certain embodiments, the gas sampling tube 108, gas cavity 110, and combustion dynamics monitoring probe 102 may all be substantially cylindrical. For example, the gas sampling tube 108 may have a diameter of approximately 0.2", 0.25", 0.3", 0.35", 0.4", 0.45", or 0.5". Furthermore, a diameter of the gas cavity 110 may be selected based on a size of the combustion dynamics monitoring probe 102 and/or the size of the aperture 104 in the flow sleeve 60. In other embodiments, the gas sampling tube 108, gas cavity 110, and combustion dynamics monitoring probe 102 may have other cross-sectional profiles that fit together.

After the combustion dynamics monitoring probe 102 is positioned within the gas sampling sleeve 100, a cap 116 may be secured into the opening 112 of the gas sampling sleeve 100 to create a seal. As will be appreciated, the seal created by the cap 116 may block a gas sample collected by the gas sampling sleeve 100 from leaking or escaping the combustor probe 84. In the illustrated embodiment, the combustion dynamics monitoring probe 102 and the gas sampling sleeve 100 are generally concentric, forming an annular gas passage 118 between the gas sampling sleeve 100 and the combustion dynamics monitoring probe 102. In other embodiments, the combustion dynamics monitoring probe 102 may be offset from the center of the gas sampling sleeve 100, forming a gas passage on one or more sides of the combustion dynamics monitoring probe 102.

As described above, the combustor probe 84 is at least partially disposed within the annulus 56 between the flow sleeve 60 and the liner 50 of the turbine combustor 14. In the illustrated embodiment, the combustor probe 84 (i.e., the combination of the combustion dynamics monitoring probe 102 and the gas sampling sleeve 100) extends a distance 120 into the annulus 56. As shown, the gas sampling tube 108 of the gas sampling sleeve 100 extends a length 122 from the flow sleeve 60 towards the liner 58. In certain embodiments, the length 122 that the gas sampling tube 108 extends into the annulus 56 is less than the length 120 that the entire combustor probe 84 extends into the annulus 56. For example, the length 122 may be approximately 25%, 30%, 35%, 40%, 45%, 50%, 55%, 60%, 65%, 70%, or 75% of the length 120 that the entire combustor probe 84 extends into the annulus 56. In certain embodiments, the length 122 may be at least approximately 50% of the length 120 that the entire combustor probe 84 extends into the annulus 56. The combustion dynamics monitoring probe 102 extends further into the annulus 56 through an opening 124 in the gas sampling tube 108 of the gas sampling sleeve 100. In the illustrated embodiment, the combustion dynamics monitoring probe 102 contacts the liner 58. However, in other embodiments, the combustion dynamics probe 102 may not extend far enough into the annulus 56 to contact the liner 58. In addition to collecting a gas sample from the annulus 56, the gas sampling tube 108 may provide additional support to the combustor dynamics monitoring probe 102. Specifically, the length 122 of the gas sampling tube 108 extending into the annulus 56 around the combustion dynamics monitoring probe 102 reduces a cantilever length 126 of the combustion dynamics monitoring probe 102 from the flow sleeve 60, thereby improving the stability of the combustion dynamics monitoring probe 102 as the pressurized air 34 flows around the combustor probe 84.

In operation, the pressurized air 34 flows through the annulus 56, and the combustor probe 84 receives a sample of the pressurized air 34 flowing through the annulus. As described above, the sample of the pressurized air 34 received by the combustor probe 84 may be directed to an analyzing system, such as the gas monitoring system 88, to analyze selected characteristics of the pressurized air 34. For example, the sample of the pressurized air 34 collected by the combustor probe 84 may be analyzed for the presence of fuel leaked by the secondary fuel system 76 in the compressor discharge 50. As described in further detail below, the gas sample from the annulus 56 is received through the opening 124 in the gas sampling tube 108 and additional apertures formed in the gas sampling tube 108. As described in detail below, the additional apertures formed in the gas sampling tube 108 may have different sizes, shapes, and configurations. The gas sample passes through the annular gas passage 118 between the gas sampling sleeve 108 and the combustor dynamics monitoring probe 102 and into the gas cavity 110. From the gas cavity 110, the gas sample exits the combustor probe 84 through a lead out port 128. In the illustrated embodiment, a gas lead 130 receives the gas sample from the gas lead out port 128 and the gas flows to the gas monitoring system 88. As described in detail below, certain embodiments of the gas sampling sleeve 100 may include more than one lead out port 128.

FIG. 4 is a cross-sectional side view of an embodiment of the gas sampling sleeve 100 of FIG. 3, illustrating apertures 150 in the gas sampling tube 108 that are configured to receive a gas sample from the annulus 56 of the turbine combustor 14. The illustrated embodiment of the gas sampling sleeve 100 includes the gas sampling tube 108 and the gas cavity 110. The gas cavity 110 is formed by a first body portion 152 and a second body portion 154, which are coupled by a first exterior transition surface 156. Further, the first body portion 152 is connected to the top portion 114 of the gas sampling sleeve 100. In certain embodiments, the probe holder 106 of FIG. 3 may abut either or both of the first and second body portions 152 and 154. The first body portion 152 also includes an interior shelf surface 158. Similarly, the second body portion 154 includes an interior shelf surface 160. In certain embodiments, either or both of the interior shelf surfaces 158 and 160 may support one or more portions of the combustion dynamics monitoring probe 102 disposed within the gas sampling sleeve 100. Furthermore, the gas sampling tube 108 is formed by a third body portion 162, which is coupled to the second body portion 154 by a second exterior transition surface 164. In certain embodiments, the second exterior transition surface 164 may abut a perimeter of the aperture 104 of the flow sleeve 60 of the turbine combustor 14. As illustrated in FIG. 4, in certain embodiments, the wall of the first body portion 152 is thicker than the wall of the second body portion 154, and the wall of the second body portion 154 is thicker than the wall of the third body portion 162.

As described above, a sample of the pressurized air 34 within the annulus 56 may be received by the gas sampling tube 108 through the opening 124 of the gas sampling tube 108, as indicated by arrow 166. Additionally, the gas sampling tube 108 includes the apertures 150 configured to receive a sample of the pressurized air 34 from the annulus 56, as indicated by arrow 168. As described in detail below, the gas sampling tube 108 may include apertures 150 in various numbers, sizes, shapes, and configurations.

As indicated by arrow 170, a gas sample received by the gas sampling tube 108 passes towards the gas cavity 110 in the gas sampling sleeve 100. The gas sample passes through the gas cavity 110, as indicated by arrow 172, and exits the gas sampling sleeve 100 through the lead out port 128, as indicated by arrow 174. As described below, the gas sampling sleeve 100 may include more than one lead out port 128. The gas lead 130 is operatively coupled to the lead out port 128 and is configured to flow the gas sample from the gas sampling tube 100 to an analyzing system, such as the gas monitoring system 88. For example, the gas monitoring system 88 may analyze the gas sample collected by the gas sampling sleeve 100 to determine if the gas sample contains fuel leaked from the secondary fuel supply system 76.

As described above, in certain embodiments, the flows 166, 168, 170, 172, and 174 flowing through the gas sampling sleeve 100 may generally flow around the combustion dynamics monitoring probe 102 (e.g., through the annular gas passage 118 between the gas sampling sleeve 108 and the combustor dynamics monitoring probe 102), which is disposed within the gas sampling sleeve 100. However, as illustrated in FIG. 4, in certain embodiments, the combustion dynamics monitoring probe 102 may be removed from within the gas sampling sleeve 100, and the gas sampling sleeve 100 may still be used to collect gas sampled from within the annulus 56 between the flow sleeve 60 and the liner 58 of the turbine combustor 14. In such embodiments, the cap 116 of FIG. 3 may be placed into the opening 112 of the gas sampling sleeve 100 to create a seal without the combustion dynamics monitoring probe 102 being disposed within the gas sampling sleeve 100.

Figure 5:
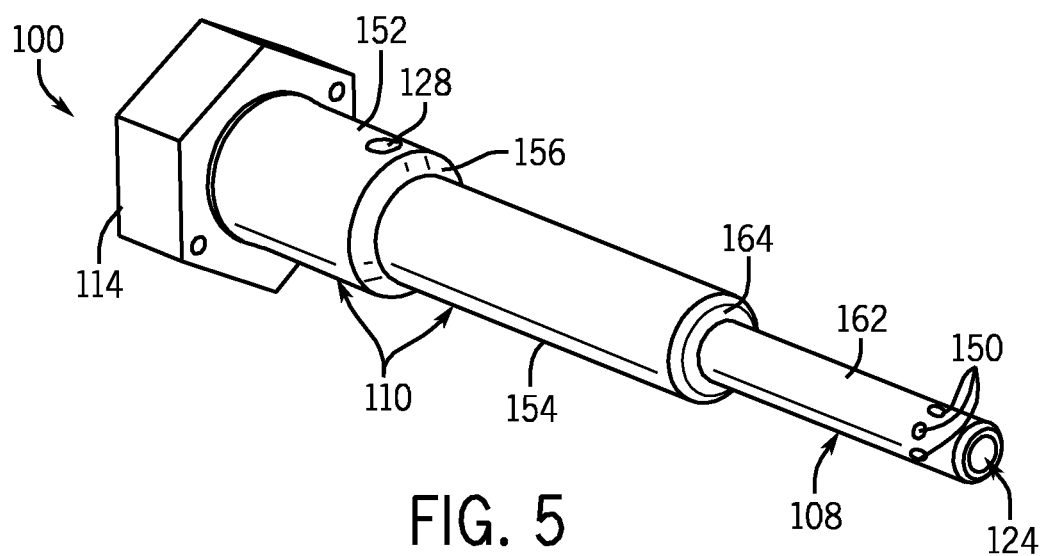
FIG. 5 is a perspective view of an embodiment of a combustor probe sleeve configured to receive a combustion dynamics monitoring probe and collect a gas sample from a combustor.

FIGS. 5-8 are perspective views of embodiments of the gas sampling sleeve 100 of FIG. 4, illustrating various numbers, shapes, sizes, and configurations of the apertures 150 in the gas sampling tube 108 for receiving a gas sample from the annulus 56 of the turbine combustor 14. The illustrated embodiments of FIGS. 5-8 include similar elements and element numbers as the embodiments of the gas sampling tube 100 illustrated in FIG. 4. FIG. 5 illustrates an embodiment of the gas sampling sleeve 100 of FIG. 4 having a single row of apertures 150 formed around the circumference of the gas sampling tube 108. Additionally, the embodiment of FIG. 5 includes a single lead out port 128, whereby a gas sample collected by the gas sampling sleeve 100 may exit the gas cavity 110 and be directed to the gas monitoring system 88 by the gas lead 120.

Figure 6:
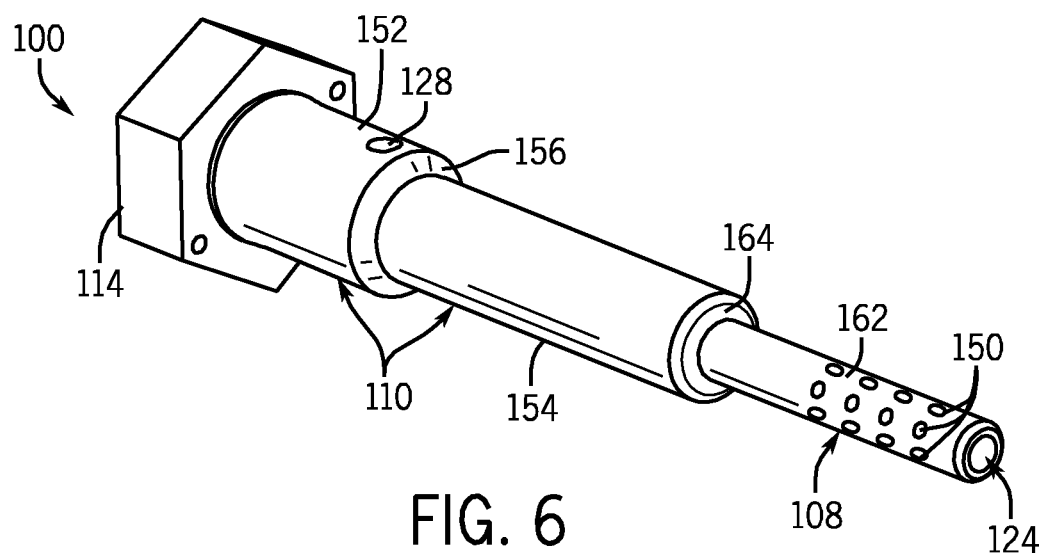
FIG. 6 is a perspective view of an embodiment of a combustor probe sleeve configured to receive a combustion dynamics monitoring probe and collect a gas sample from a combustor.
Figure 7:
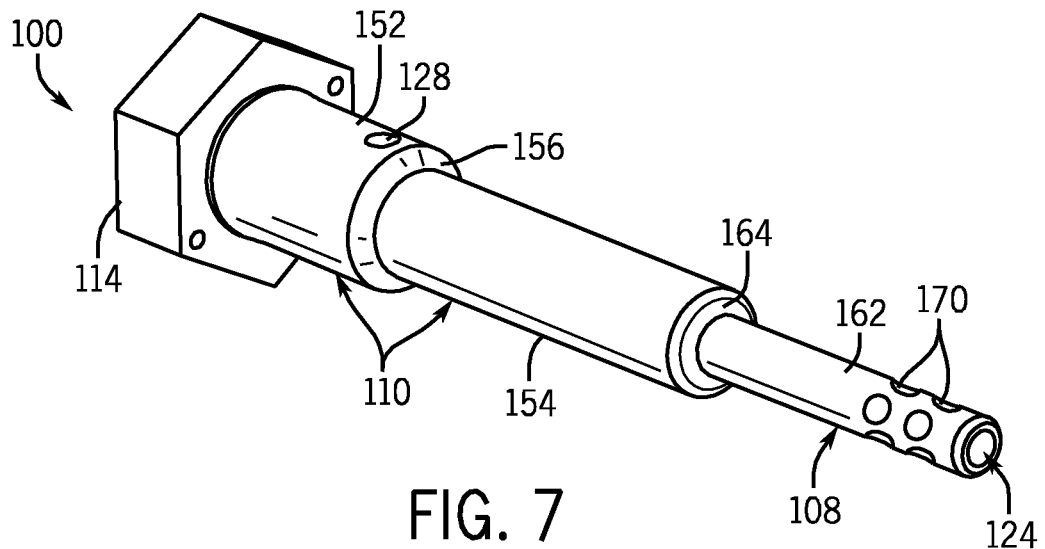
FIG. 7 is a perspective view of an embodiment of a combustor probe sleeve configured to receive a combustion dynamics monitoring probe and collect a gas sample from a combustor.

FIG. 6 illustrates an embodiment of the gas sampling sleeve 100 of FIG. 4 having four rows of apertures 150 formed around the circumference of the gas sampling tube 108. Although illustrated as having four rows of apertures, in other embodiments, the gas sampling sleeve 100 may have two, three, five, six, or even more rows of apertures 150. Forming additional apertures 150 around the gas sampling tube 108 may be beneficial for collecting greater gas sample volumes. Similarly, gas samples may be collected at an increased rate with embodiments of the gas sampling sleeve 100 having additional apertures 150. For example, the apertures 150 may be spaced across the entire length of the gas sampling tube 108. In certain embodiments, the apertures 150 may be evenly spaced across the gas sampling tube 108, or the apertures 150 may have variable spacing along the length of the gas sampling tube 108. Furthermore, additional apertures 150 may be formed in other configurations (i.e., other than row configurations). For example, certain embodiments may include apertures 150 formed in an offset configuration, or in a random configuration. FIG. 7 illustrates an embodiment of the gas sampling sleeve 100 of FIG. 4 having larger sized apertures 170 formed around the circumference of the gas sampling tube 108. As will be appreciated, the larger sized apertures 170 may be beneficial in increasing the volume and rate at which gas samples are collected by the gas sampling sleeve 100.

Figure 8:
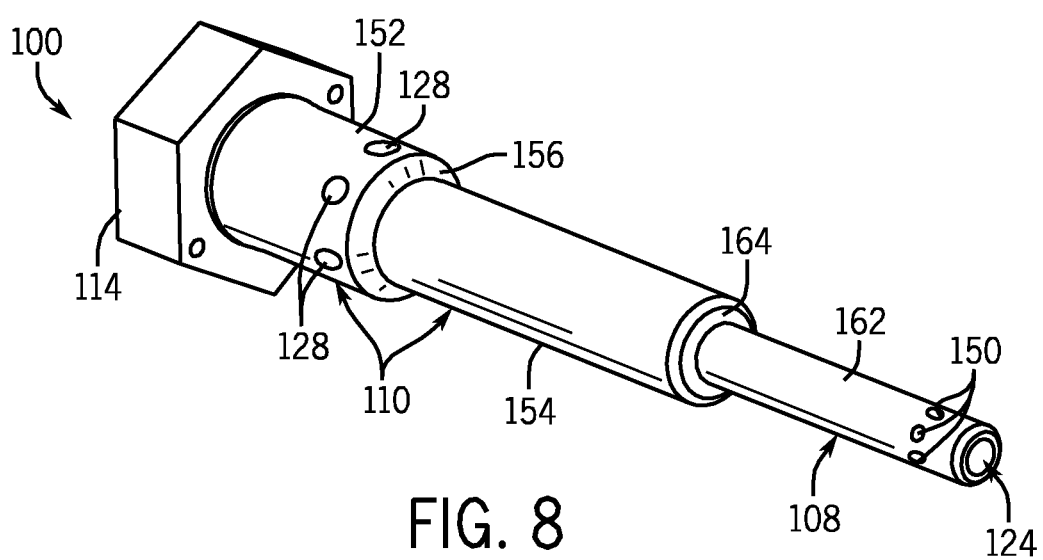
FIG. 8 is a perspective view of an embodiment of a combustor probe sleeve configured to receive a combustion dynamics monitoring probe and collect a gas sample from a combustor.

FIG. 8 illustrates an embodiment of the gas sampling sleeve 100 of FIG. 4 having additional lead out ports 128. Each lead out port 128 may be operatively coupled to a separate gas lead 130 for routing gas samples collected by the gas sampling sleeve 100 to an analyzing system, such as the gas monitoring system 88. As with the additional apertures 150 and the larger sized apertures 170 in the illustrated embodiments of FIGS. 6 and 7, the additional lead out ports 128 may be beneficial in increasing the volume and rate at which gas samples are collected by the gas sampling sleeve 100 from the annulus 56 of the turbine combustor 14. Furthermore, in certain embodiments, each gas lead 130 operatively coupled to a respective lead out port 128 may be connected to a different gas monitoring system 88. For example, one gas lead 130 may be connected to a gas monitoring system 88 configured to detect the presence of fuel in a gas sample collected by the gas sampling sleeve 100. Another gas lead 130 may be connected to a gas monitoring system 88 configured to analyze the composition of a gas sample collected by the gas sampling sleeve 100. Still another gas lead 130 may be connected to a gas monitoring system 88 configured to determine the temperature of a gas sample collected by the gas sampling sleeve 100. In this manner, multiple gas samples may be collected by the gas sampling sleeve 100, and different specialized gas monitoring systems 88 may be used to analyze different characteristics of the gas samples collected. Alternatively, each of the gas monitoring systems 88 may be configured to analyze the same characteristics of the gas samples collected by the gas sampling sleeve 100. In either application, if one gas monitoring system 88 needs to be shut down for repair or replacement, the remaining gas monitoring systems 88 may continue operating to analyze gas samples collected by the gas sampling sleeve 100.

The dual purpose combustor probe 84 having the gas sampling sleeve 100 and the combustion dynamics monitoring probe 102 provides a system for monitoring the combustion dynamics of the turbine combustor 14 as well as the composition of the pressurized air 34 within the annulus 56 between the flow sleeve 60 and the liner 58 of the turbine combustor 14 with a single probe assembly. This may be beneficial for turbine combustors 14 having a LLI system, where a fuel is routed through the compressor discharge 50. Specifically, an existing probe port may be retrofitted with the combustor probe 84 including the gas sampling sleeve 100, allowing for the detection of fuel within the pressurized air 34 received from the compressor discharge 50.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A system, comprising:
    a turbine combustor;
    a combustor probe, comprising:
        a combustion dynamics monitoring probe configured to monitor combustion dynamics within the turbine combustor; and
        a gas sampling sleeve disposed about the combustion dynamics monitoring probe and configured to collect a gas sample from an airflow path between a liner and a flow sleeve of the turbine combustor; and
        a combustor probe holder configured to mount the combustor probe within a probe port of the flow sleeve; and
    a gas monitoring system coupled to the gas sampling sleeve, wherein the gas monitoring system is configured to receive and analyze the gas sample.

2. The system of claim 1, wherein the combustion dynamics monitoring probe comprises a wave guide.

3. The system of claim 1, wherein the gas sampling sleeve comprises a gas sample tube and a gas sample cavity operatively coupled to the gas sample tube.

4. The system of claim 3, wherein the gas sample tube includes at least one aperture configured to receive the gas sample from the airflow path.

5. The system of claim 3, wherein the gas sample cavity includes at least one lead out port configured to output the gas sample.

6. The system of claim 1, wherein the combustion dynamics monitoring probe is disposed within the gas sampling sleeve forming an annular passage between the combustion dynamics monitoring probe and the gas sampling sleeve.

7. The system of claim 1, wherein the combustion dynamics monitoring probe and the gas sampling sleeve are concentric.

8. The system of claim 1, wherein the combustor probe at least partially enters an airflow passage between the liner and the flow sleeve of the turbine combustor.

9. The system of claim 1, wherein the probe port is located near a head end of the turbine combustor.

10. The system of claim 1, wherein the gas sampling sleeve extends at least approximately 50% of a radial distance between the flow sleeve and the liner, and the combustion dynamics monitoring probe contacts the liner.

11. The system of claim 1, wherein the gas monitoring system is configured to detect a presence of fuel in the gas sample, measure a composition of the gas sample, measure a temperature of the gas sample, or any combination thereof.

12. A system, comprising:
    a probe holder configured to mount to a flow sleeve of a turbine combustor;
    a gas sampling sleeve configured to collect a gas sample from an air flow in the turbine combustor, wherein the gas sampling sleeve is disposed within the probe holder;
    a combustion dynamics probe configured to monitor combustion dynamics in the turbine combustor, wherein the combustion dynamics probe is disposed within the gas sampling sleeve, and an annular passage is disposed between the combustion dynamics probe and the gas sampling sleeve; and
    a gas monitoring system coupled to the gas sampling sleeve, wherein the gas monitoring system is configured to receive and analyze the gas sample.

13. The system of claim 12, wherein the gas sampling sleeve and the combustion dynamics probe are concentric.

14. The system of claim 12, wherein the gas sampling sleeve comprises a sampling tube and a sample cavity, wherein the sampling tube and the sample cavity are operatively connected.

15. The system of claim 14, wherein the sampling tube includes at least one sampling aperture configured to receive the gas sample from the air flow in a passage in the turbine combustor.

16. The system of claim 15, wherein the passage is an airflow passage between the flow sleeve and a liner of the turbine combustor.

17. The system of claim 14, wherein the sample cavity includes at least one lead out port configured to output the gas sample collected by the gas sampling sleeve; and wherein the system comprises a gas lead extending from the at least one lead out port to the gas monitoring system.

18. A system, comprising:
    a combustor probe;
    a gas sampling tube operatively coupled to a gas sample cavity, wherein the gas sampling tube and the gas sample cavity are configured to receive the combustor probe and to collect a gas sample from an air flow in a turbine combustor, and wherein the gas sampling tube comprises a plurality of apertures configured to direct the gas sample from the air flow in the turbine combustor to the gas sample cavity;
    a gas monitoring system, wherein the gas monitoring system is configured to receive and analyze the gas sample; and
    a gas lead extending from a lead out port of the gas sample cavity to the gas monitoring system, wherein the gas lead is configured to flow the gas sample from the gas sample cavity to the gas monitoring system.

19. The system of claim 18, wherein the plurality of apertures are formed about a circumference of the gas sampling tube.

20. The system of claim 18, wherein the gas monitoring system is configured to detect a presence of fuel in the gas sample, measure a composition of the gas sample, measure a temperature of the gas sample, or any combination thereof.

* * * * *

UNITED STATES PATENT AND TRADEMARK OFFICE
CERTIFICATE OF CORRECTION

PATENT NO. : 8,997,558 B2  
APPLICATION NO. : 13/075055  
DATED : April 7, 2015  
INVENTOR(S) : Romig et al.

Page 1 of 1

It is certified that error appears in the above-identified patent and that said Letters Patent is hereby corrected as shown below:

In the Drawings

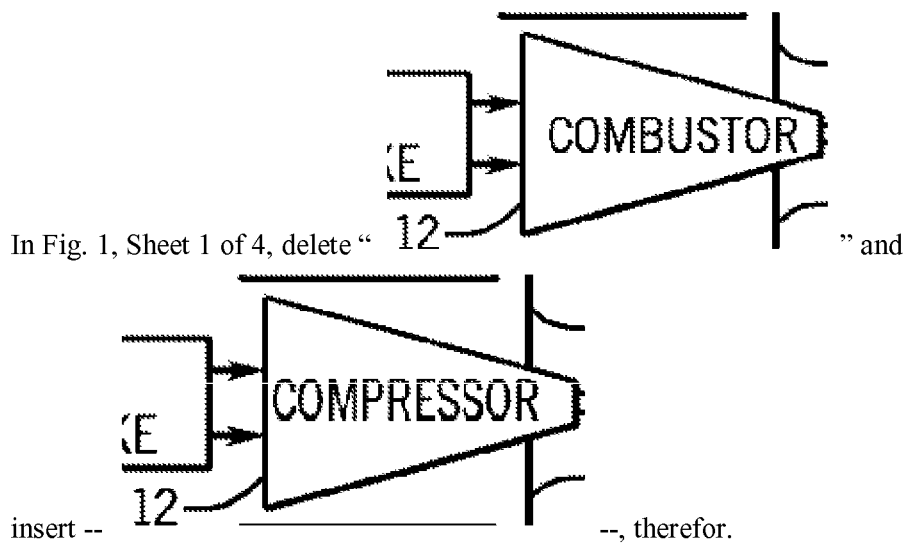

In Fig. 1, Sheet 1 of 4, delete " " and insert -- -- , therefor.

In the Specification

In Column 6, Line 12, delete "liner 50" and insert -- liner 58 --, therefor.

Signed and Sealed this  
Thirty-first Day of May, 2016

Michelle K. Lee  
*Director of the United States Patent and Trademark Office*